United States Patent [19]
Glagovsky et al.

[11] 3,978,711
[45] Sept. 7, 1976

[54] METHOD OF TESTING WEAR RESISTANCE OF ARTICLES ON THE BASIS OF POLYCRYSTALLINE CUBIC BORON NITRIDE

[76] Inventors: Boris Aronovich Glagovsky, prospekt M. Toreza, 15, kv. 49, Leningrad; Anatoly Samoilovich Kamenkovich, ulitsa Tashkentskaya, 15/22, kv. 123, Moscow; Vladislav Sergeevich Lysanov, ulitsa Vavilovykh, 15/3, kv. 7, Leningrad; Igor Borisovich Moskovenko, Kirovsky prospekt, 50, kv. 6, Leningrad; Garri Shmilevich Roitshtein, Kirovsky prospekt, 65, kv. 9, Leningrad; Ljudmila Yakovlevna Slavina, prospekt Shvernika, 16, kv. 80, Leningrad; Leon Izrailevich Feldgun, Ligovsky prospekt, 3/9, kv. 13, Leningrad; Larisa Ruvimovna Frenkel, ulitsa Butlerova, 12, kv. 193, Leningrad; Alexandr Lazarevich Khait, prospekt Maklina, 34, kv. 21, Leningrad; Galina Alexandrovna Shashkina, Kirovsky prospekt, 54, kv. 57, Leningrad; Veniamin Alexandrovich Yashin, prospekt Engelsa 70, kv. 37, Leningrad; Zinovy Illich Kremen, Tikhoretsky propspekt, 10, korpus 2, kv. 54., all of Leningrad; Yakov Abramovich Muzykant, ulitsa Chusoyskaya, 11, korpus 5, kv.1 113, Moscow, all of U.S.S.R.

[22] Filed: Aug. 20, 1975

[21] Appl. No.: 606,104

Related U.S. Application Data

[63] Continuation of Ser. No. 415,902, Nov. 14, 1973, abandoned.

[30] Foreign Application Priority Data

Nov. 4, 1972   U.S.S.R. .......................... 1847757

[52] U.S. Cl. .............................................. 73/67.2
[51] Int. Cl.$^2$ ........................................ G01N 29/00
[58] Field of Search ................ 73/7, 67, 67.1, 67.2, 73/67.5 R

[56] References Cited
UNITED STATES PATENTS

| | | | |
|---|---|---|---|
| 3,003,352 | 10/1961 | Ziegler et al. | 73/67.5 R |
| 3,603,136 | 9/1971 | Diamond et al. | 73/67.8 R |
| 3,690,155 | 9/1972 | Eichler | 73/67.5 R |

*Primary Examiner*—Jerry W. Myracle
*Attorney, Agent, or Firm*—Hoiman & Stern

[57] ABSTRACT

A method of testing wear-resistance of articles which comprises measuring the rate of propagation of ultrasonic oscillations in a reference article which has the lowest admissible wear resistance. The rate of propagation of ultrasonic oscillations in the articles being tested is compared with the rate in the reference article. The reference article is placed into a liquid in the suspended state and the articles being tested are placed into the same liquid. Those articles, which ascend to the surface, are rejected.

5 Claims, 1 Drawing Figure

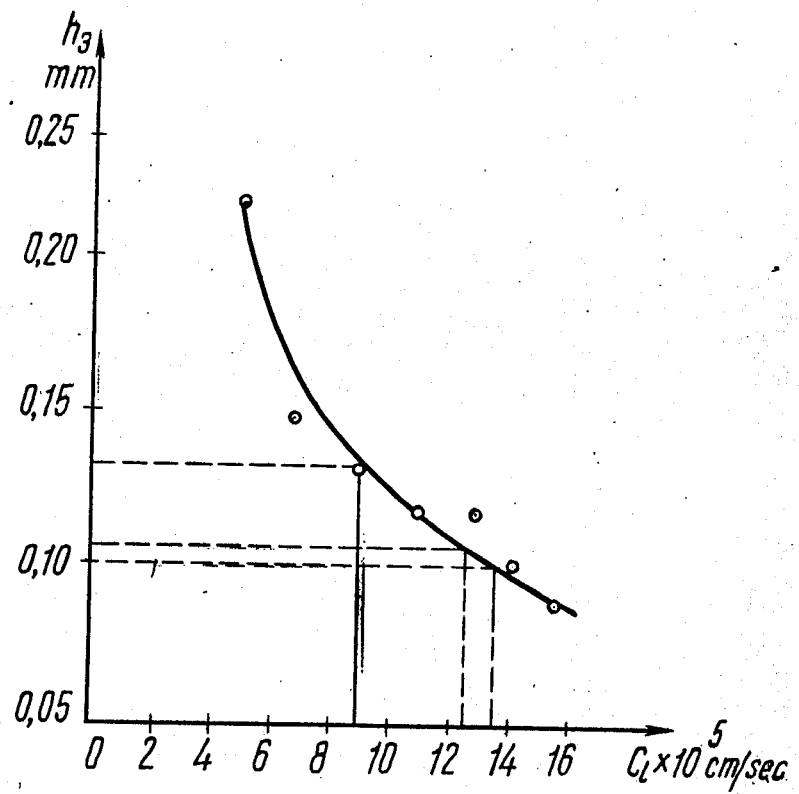

METHOD OF TESTING WEAR RESISTANCE OF ARTICLES ON THE BASIS OF POLYCRYSTALLINE CUBIC BORON NITRIDE

This is a continuation of application Ser. No. 415,902 filed Nov. 14, 1973, now abandoned.

BACKGROUND OF THE INVENTION

The present invention relates to the improvement of methods for testing articles made of superhard materials, and more particularly is concerned with a method for testing wear resistance of articles on the basis of polycrystalline cubic boron nitride and may be the most efficiently used in rejecting blanks for the manufacture of cutting tools.

The wear resistance of a tool is characterized by the value of $h_z$ of a trailing edge of a tool in millimeters under predetermined machining conditions during a predetermined time period, and the greater the wear $h_z$, the lower wear resistance. The term "the lowest admissible wear resistance value" means herein that wear resistance which ensures a predetermined productivity with a predetermined accuracy class and surface finish.

Methods for testing wear resistance of articles heretofore known are based upon mechanical destruction (abrasion) of a part of the article and measurement of the amount of wear which characterizes the wear resistance. The most reliable results are obtained by performing test turning using for that purpose the tools made of the articles being tested. In this case the turning is by means of turning tools under conditions most similar to the operating conditions which will be met by the articles. The amount $(h_z)$ measuring the tool wear over the trailing edge thereof is used as a value for characterizing the wear resistance of the article.

The disadvantages of known methods consist in that they permit evaluation of the wear resistance for only a portion of the article, under test and not for the article as a whole. Also reproduction of the test results is not possible and the known methods are rather labour-consuming.

In addition, it should be noted that the above-described method is the destructive method and is selective since testing of the wear resistance of only a sample of the tested number of articles is possible.

Therefore, the above described known methods do not provide a reliable test of articles which eliminates the possibility of subgrade articles being shipped to a purchaser.

SUMMARY OF THE INVENTION

It is an object to the present invention to provide a non-destruction method for testing the wear resistance of articles.

Another object of the invention is to improve the speed of testing the wear resistance of articles made of cubic boron nitride.

Other objects of the invention consist in improving the reliability of testing, the possibility of testing every article and the automation of the test process.

These and other object are accomplished in a method for testing the wear resistance of articles on the basis of polycrystalline cubic boron niride wherein according to the invention the rates of propagation of ultrasonic oscillations in the articles being tested are compared the rate of propagation of ultrasonic oscillations in a reference article having the lowest admissible wear resistance value, so that the articles having a rate of propagation of ultrasonic oscillations lower than that of the reference article are rejected.

The advantage of the invention resides in the fact that the method herein contemplated is a non-destructive test of the wear resistance of the blanks prior to manufacture of cutting tools therefrom. In addition, the present method provides for the mass-scale testing of articles made of cubic boron nitride.

According to the simplest embodiment of the invention the wear resistance test may be conducted by the following method, wherein according to the invention in order to compare the rates of propagation of ultrasonic oscillations, the reference article is placed into a receptacle containing liquid of a density such as the reference article should be suspended between the upper and lower levels of the liquid, whereafter a group of the articles being tested is placed into the same receptacle, and the articles, which ascend to the surface of the liquid, have the wear resistance greater than that of the reference article.

In order to improve the test quality, it is desirable to subject the reference article and the articles being tested to an ultrasonic treatment prior to the placing into the liquid in a medium which is active with respect to hexagonal boron nitride.

The active medium may comprise a 50–70 percent solution of alkali or ethyl alcohol, and the treatment is preferably conducted for 30–60 minutes with an intensity of ultrasonic oscillations of at least 4 W/cm$^2$.

BRIEF DESCRIPTION OF THE DRAWINGS

In some cases the wear resistance may be determined from the accompanying drawing showing a graph of wear of a blank of material versus propagation of ultrasonic oscillations through the blank.

The invention will now be described in detail with reference to different embodiments of the method of testing blanks made of polycrystalline cubic boron nitride to be used for the manufacture of cutting tools, as well as to the drawing of wear v.rate of propagation of ultrasonic oscillations.

DETAILED DESCRIPTION OF PREFERRED EMBODIMENTS

The method of testing wear resistance of articles made of cubic boron nitride is based upon the relationship which has been revealed by the inventors according to which when the wear of an article is greatest, the rate of propagation of ultrasonic oscillations in a blank (or cutting tool) made of cubic boron nitride is the lowest.

A large number of experiments have been conducted to establish this relationship. The essence of these experiments consists in the following:

By using an arrangement for measuring the resonance frequency, the natural frequency of the blanks is measured, and then on the basis of the blank dimensions the rate of propagation of the ultrasonic oscillations is determined by conventional methods.

The arrangement for measuring the resonance frequency may comprise the arrangement disclosed in U.S. patent No. 3,499,318. This arrangement comprises a radiator and a receiver of ultrasonic oscillations having a frequency-controlled ultrasonic generator, and amplifier and a resonance indicator. The article being tested was placed in the above-described arrangement. By varying the frequency of the excitation ultrasonic oscillations, resonance is established between the excitation oscillations and the natural torsional or bending oscillations of the article at which the frequencies of the natural and excitation oscillations are equal. The frequency of the excitation oscillations is determined from the setting dial of the generator. Then the geometrical dimensions of the blank are measured and, as mentioned above, the rate of propagation of elastic waves in the blanks is determined from known relationships.

Turning tools are then made of the blanks, and these tools are tested in cutting highly-tempered steel with a hardness 60–64 on the Rockwell scale under the following cutting conditions: $v = 80$ m/s, $S=0.04$ mm/double-stroke, $t=0.2$ mm, turning time — 5 minutes. After turning has been completed, the wear in the tools is measured at the trailing edge by using a microscope. The results of these measurements are used to plot a graph of wear v.rate of propagation of ultrasonic oscillations in the blanks, wherein the rate of propagation of ultrasonic oscillations in the blanks (in $10^{-5}$ cm/s) is plotted on the abscissa, while the wear values for tools made of these blanks are plotted on the ordinates. This graph shows that the greater the rate of propagation of ultrasonic oscillations in the blank, the lower the wear thereof.

Experiments conducted under other cutting conditions have shown that generally the shape of the graph will change insignificantly. This permits, the graph to be directly used when extremely stringent requirements as to the accuracy of the wear resistance test are not necessary. In these cases it is sufficient to measure the rate of propagation of the ultrasonic oscillations in the article being tested and to determine from the diagram its wear resistance. In practice the wear resistance may be tested by using the method according to the invention in different ways as follows.

EXAMPLE 1

A reference article is made of cubic boron nitride under conditions which ensure that the article has the lowest admissible resistance to wear. Such an article may be obtained under laboratory conditions. According to the preferred embodiment of the invention several such reference articles are made, whereafter the rate of propagation of ultrasonic oscillations is determined for each of them. A part of the articles is tested in the form of turning tools under predetermined operating conditions and their resistance to wear is then determined. Then these blanks having a rate of propagation of ultrasonic oscillations similar to that of the blank which exhibited the lowest admissible wear resistance during the test, is found by way of selection. The selected blank the reference blank and may be used for subsequent operations. During the test the rate of propagation of ultrasonic oscillations is measured in the blank being tested, and this rate is compared with the rate of propagation of ultrasonic oscillations in the reference article. The articles exhibiting the rate of propagation of ultrasonic oscillations which is greater than the rate of propagation of ultrasonic oscillations in the reference article have the wear resistance greater than that mininal admissible.

EXAMPLE 2

The reference article is determined as described in Example 1. The reference article and the articles being tested are subjected to an ultrasonic treatment at a an intensity of ultrasonic oscillations of at least 4 W/cm² in a medium which is active with respective to hexagonal boron nitride. This medium may comprise a 50–70 percent solution of alkali or ethyl alcohol. The treatment is conducted for 30–60 minutes.

After the treatment the articles under test and the reference article are washed and dried.

Liquid having a density greater than that of the articles being tested is then poured into a receptacle. The reference article is placed into the liquid, and distilled water is added under careful stirring to obtain a liquid having a density such that the reference article is suspended between the lower and upper levels of the liquid.

The articles under test are pthen placed into the liquid, the articles ascending to the surface are rejected, since they have smaller rate of propagation of ultrasonic oscillations, and therefore lower wear resistance than the reference article.

The present invention ensures a high-speed one hundred-percent test of wear resistance which is one of the basic parameters of articles made of polycrystalline cubic boron nitride, and the test is highly accurate.

What is claimed is:

1. A method of testing the wear resistance of articles based on the physical properties of polycrystalline cubic boron nitride, comprising the steps of: measuring the rate of propagation of ultrasonic oscillations in a reference article made from cubic boron nitride and having a predetermined resistance to wear equal to the lowest admissible value thereof; comparing the rate of propagation of ultrasonic oscillations in each of the articles being tested with the rate of propagation of ultrasonic oscillations in said reference article; rejecting those articles of the articles being tested having a rate of propagation of ultrasonic oscillations lower than the rate of propagation of ultrasonic oscillations in the reference article.

2. A method according to claim 1, wherein before the step of comparing the rate of propagation of ultrasonic oscillations between each of the articles being tested and the reference article, the reference article is placed into a liquid having a density such that the reference article is suspended between the upper and lower levels thereof, whereafter the articles being tested are placed into said liquid, and those articles of the articles being tested, which ascend to the surface of the liquid, have a resistance to wear less than that of the reference article.

3. A method according to claim 2, wherein prior to placing the articles being tested and the reference article into said liquid, the reference article and the articles being tested are subjected to an ultrasonic treatment in a medium which is active with respect to hexagonal boron nitride.

4. A method according to claim 3, wherein the reference article and the articles being tested are subjected to a treatment in a 50–70 percent solution of alkali or ethyl alcohol for 30–60 minutes under ultrasonic oscillations having an intensity of at least 4 W/cm².

5. A method of testing the wear resistance of articles on the basis of polycrystalline cubic boron nitride comprising the steps of: measuring the rate of propagation of ultrasonic oscillations in each of the articles being tested; and comparing the measured rate of propagation to a graph depicting the wear of blanks formed of boron nitride v. the rate of propagation of ultrasonic oscillations through said blanks to ascertain the value of wear resistance of each of the articles.

* * * * *